United States Patent
Xu et al.

(10) Patent No.: US 10,925,678 B2
(45) Date of Patent: Feb. 23, 2021

(54) OPTICAL TRACKING TOOL FOR NAVIGATING SURGERY

(71) Applicant: TINAVI Medical Technologies Co., Ltd., Beijing (CN)

(72) Inventors: Jin Xu, Beijing (CN); Yun Feng, Beijing (CN)

(73) Assignee: TINAVI MEDICAL TECHNOLOGIES CO., LTD., Beijing (CN)

( * ) Notice: Subject to any disclaimer, the term of this patent is extended or adjusted under 35 U.S.C. 154(b) by 183 days.

(21) Appl. No.: 15/756,355

(22) PCT Filed: Aug. 25, 2016

(86) PCT No.: PCT/CN2016/096661
§ 371 (c)(1),
(2) Date: Feb. 28, 2018

(87) PCT Pub. No.: WO2017/036340
PCT Pub. Date: Mar. 9, 2017

(65) Prior Publication Data
US 2018/0250077 A1    Sep. 6, 2018

(30) Foreign Application Priority Data
Aug. 31, 2015 (CN) .......................... 201510547376.9

(51) Int. Cl.
*A61B 34/20* (2016.01)
*A61B 34/30* (2016.01)
(Continued)

(52) U.S. Cl.
CPC .............. *A61B 34/20* (2016.02); *A61B 34/30* (2016.02); *A61B 90/39* (2016.02); *A61B 34/25* (2016.02);
(Continued)

(58) Field of Classification Search
CPC ....................... A61B 2034/2055; A61B 34/20
See application file for complete search history.

(56) References Cited

U.S. PATENT DOCUMENTS 7,945,311 B2 * 5/2011 McCloy .................... G01S 5/16
600/424
2004/0167393 A1    8/2004 Solar et al.
(Continued)

FOREIGN PATENT DOCUMENTS

CN    201067403 Y    6/2008
CN    102258399 A    11/2011
(Continued)

OTHER PUBLICATIONS

ISA State Intellectual Property Office of the People's Republic of China, International Search Report Issued in Application No. PCT/CN2016/096661, dated Nov. 14, 2016, WIPO, 6 pages.

*Primary Examiner* — Gary Jackson
*Assistant Examiner* — Anant A Gupta
(74) *Attorney, Agent, or Firm* — McCoy Russell LLP

(57) ABSTRACT

Provided is an optical tracking tool for navigating a surgery, comprising a mounting base. The mounting base is provided with two to six supporting faces thereon. Two or four reflective balls are arranged on each of the supporting faces. A positioning surface is formed by the four reflective balls located on the same supporting face or the four reflective balls respectively located on two adjacent supporting faces. An included angle between surface normal vectors of two adjacent positioning surfaces is 90°-140°. As compared with a tracking tool having a single positioning surface formed by four reflective balls in the prior art, the optical tracking tool can considerably broaden an effective tracking range of a system, thereby improving system accuracy.

2 Claims, 2 Drawing Sheets

(51) Int. Cl.
*A61B 90/00* (2016.01)
*A61B 34/00* (2016.01)

(52) U.S. Cl.
CPC ............... *A61B 2034/2055* (2016.02); *A61B 2090/3983* (2016.02)

(56) References Cited

U.S. PATENT DOCUMENTS

2007/0085496 A1* 4/2007 Philipp ............ A61B 17/32002
318/139
2008/0009697 A1* 1/2008 Haider .................. A61B 90/11
600/407
2011/0046636 A1* 2/2011 Wu ........................ A61B 90/39
606/130

FOREIGN PATENT DOCUMENTS

| | | | |
|---|---|---|---|
| CN | 105147395 | A | 12/2015 |
| CN | 205054433 | U | 3/2016 |
| TW | 201106916 | A | 3/2011 |
| WO | 2013115640 | A1 | 8/2013 |

\* cited by examiner

OPTICAL TRACKING TOOL FOR NAVIGATING SURGERY

CROSS-REFERENCE TO RELATED APPLICATIONS

The present application is a U.S. National Phase of International Patent Application Serial No. PCT/CN2016/096661, entitled "OPTICAL TRACKING TOOL FOR NAVIGATING SURGERY," filed on Aug. 25, 2016. International Patent Application Serial No. PCT/CN2016/096661 claims priority to Chinese Patent Application No. 201510547376.9, filed on Aug. 31, 2015. The entire contents of each of the above-cited applications are hereby incorporated by reference in their entirety for all purposes.

TECHNICAL FIELD

The present invention relates to an optical tracking tool for navigating a surgery, belonging to the technical field of computer-aided surgery.

RELATED PRIOR ART

Currently, the optical tracking device used clinically for navigating a surgery is mainly an optical positioning and tracking system manufactured by NDI Company of Canada. The positioning principle of this type of system is that: infrared light emitted by a binocular position sensor reaches a surgical device or instrument equipped with a tracking tool, and a small ball (also called a reflective ball or lens) on the tracking tool, capable of reflecting infrared light, can reflect the infrared light back to the position sensor, and hereby the built-in software of the system calculate to obtain the position coordinates of the tracking tool (including the position and angle of the tracking tool), so as to realize positioning and tracking of the corresponding surgical device and instrument.

According to the aforementioned positioning principle of the system, the tracking tool is a component that plays a critical role in the tracking of the surgical devices and instruments. The accuracy of the position coordinates of the tracking tool, calculated by the system, determines the accuracy of the surgical navigation system. Tracking tools commonly used at present include 3 to 4 coplanar (which is known as the positioning face) reflective balls. The tracking tool, disclosed in Chinese patent application CN200720012127.0, only has one positioning face. The main disadvantage of this design is that the tracking range of the system is small, usually less than ±90°. Moreover, as the accuracy of the position coordinates of the tracking tool, obtained by the optical tracking system, is related to the angle defined by the positioning face of the tracking tool and the optical axis of the binocular position sensor, the greater the angle, the worse the accuracy, and the accuracy of a surgical navigation system using the tracking tool is difficult to be guaranteed.

SUMMARY OF THE INVENTION

In view of the above problems, an object of the present invention is to provide an optical tracking tool for navigating a surgery, with a high positioning accuracy and a large tracking range.

To achieve the above object, the present invention adopts the following technical solutions: an optical tracking tool for navigating a surgery, comprising a mounting base, wherein the mounting base is provided with two to six supporting faces thereon, two or four reflective balls are mounted on each of the supporting faces, a positioning face is formed by four reflective balls located on the same supporting face or four reflective balls located on two adjacent supporting faces, and an included angle between surface normal vectors of two adjacent positioning faces is 90°-140°.

The reflective balls and the supporting surfaces are connected through a reflective ball mounting base; the reflective ball mounting base comprises a ball support, a seal rubber ring and an annular cover plate, and the ball support is fixedly connected to the supporting face; the reflective ball is composed of two hemispheres with different diameters, wherein the larger-diameter hemispherical portion of the reflective ball is held up by the ball support and then is locked and fastened by the annular cover plate arranged on the ball support in a form of a buckle, the smaller-diameter hemispherical portion of the reflective ball protrudes from the annular cover plate, and the seal rubber ring is arranged between the ball support and the larger-diameter hemisphere portion of the reflective ball.

The mounting base is provided with an interface to be connected with a surgical tool and/or a surgical robot.

Due to adopting the above technical solution, the present invention has the following advantages: 1. compared with a tracking tool having a single positioning face formed by four reflective balls in the prior art, the optical tracking tool can obviously broaden an effective tracking range of a system, thereby improving system accuracy; 2. the present invention provides a connection structure for the reflective balls and the supporting faces, which can realize the precise positioning and connection between the reflective balls and the supporting faces; 3. the present invention, with simple structure and reliable performance, can be widely used in tracking and positioning of clinical surgical robots.

BRIEF DESCRIPTION OF THE DRAWINGS

The present invention is described in detail below with reference to the accompanying drawings. However, it should be understood that the drawings are provided only for the purpose of providing a better understanding of the present invention, and are not to be construed as a limit to the present invention.

DETAILED DESCRIPTION

The present invention is described in detail below with reference to the accompanying drawings and embodiments.

Embodiment 1

Figure 1:
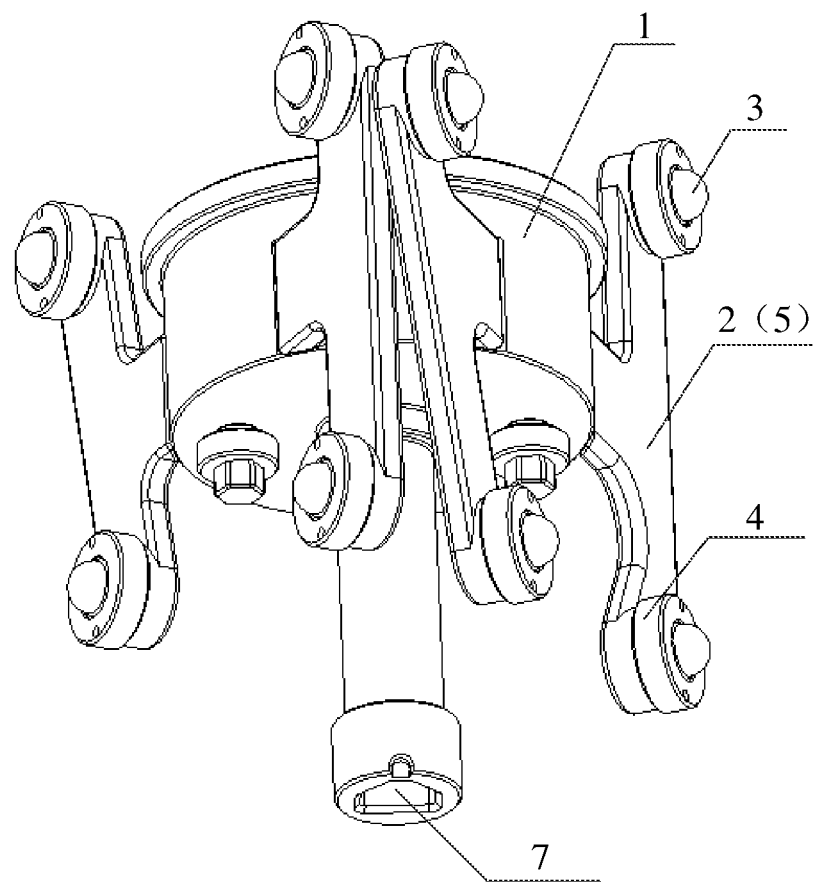
FIG. 1 is a schematic structural diagram of Embodiment 1.

As shown in FIG. 1, this embodiment includes a mounting base 1 configured to be connected with an instrument at a tail end or a front end of the robot; two supporting faces 2 are arranged on the mounting base 1, four reflective balls 3 are mounted on each of the supporting faces 2, and each of the reflective balls 3 is fixed on the corresponding supporting face 2 through a reflective ball mounting base 4. In this embodiment, a positioning face 5 is formed by a quadrilateral with the four reflective balls 3 on the same supporting face 2 as end points. The included angle between the surface normal vectors of the two adjacent positioning faces 5 is 90°-140°, and the two positioning faces 5 are different in shape or size.

Figure 2:
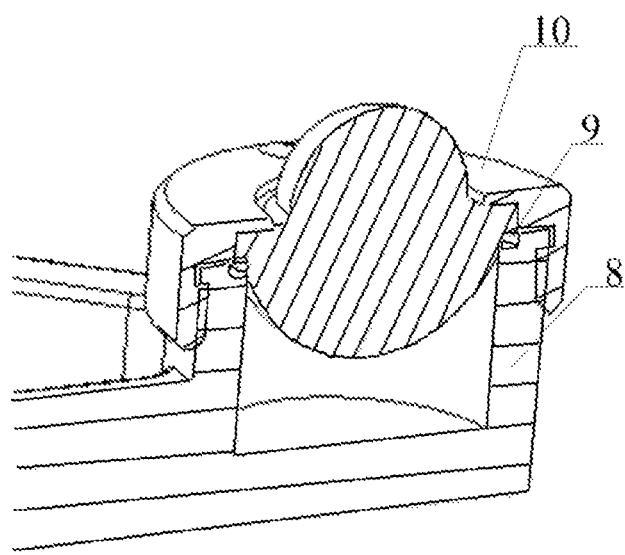
FIG. 2 is a schematic structural diagram of Embodiment 1.

As shown in FIG. 2, the reflective ball mounting base 4 includes a ball support 8, a seal rubber ring 9 and an annular cover plate 10, wherein the ball support 8 is fixedly connected to the supporting face 2. In this embodiment, each of the reflective balls 3 is composed of two hemispheres with different diameters, wherein the larger-diameter hemispherical portion is held up by the ball support 8 and then is locked and fastened by the annular cover plate 10 arranged on the ball support 8 in a form of a buckle, and the smaller-diameter hemispherical portion protrudes from the annular cover plate 10; and a seal rubber ring 9 is arranged between the ball support 8 and the larger-diameter hemisphere portion.

Embodiment 2

Figure 3:
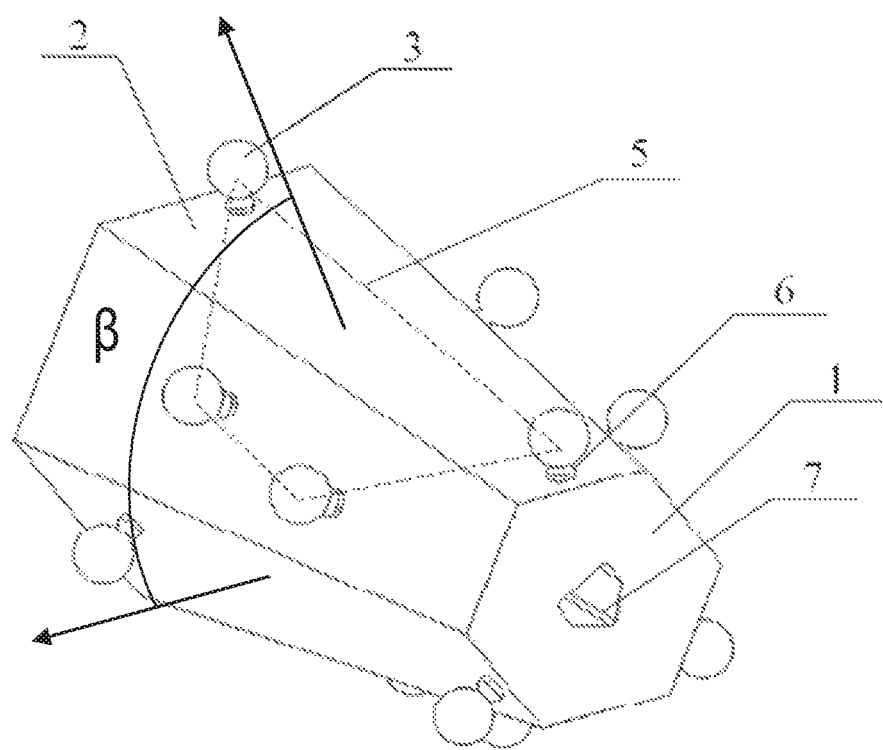
FIG. 3 is a schematic structural diagram of Embodiment 2.

As shown in FIG. 3, this embodiment includes a mounting base 1 used to be connected with an instrument at a tail end or a front end of the robot; six supporting faces 2 are arranged on the mounting base 1, two reflective balls 3 are mounted on each of the supporting faces 2, each of the reflective balls 3 is connected to a corresponding supporting face 2 through a mounting column 6. In this embodiment, a positioning face 5 is formed by a quadrilateral with the four reflective balls 3 on the two adjacent supporting faces 2 as end points. The included angle β between the surface normal vectors of the two adjacent positioning faces 5 is 90°-140°, and any two positioning faces 5 are different in shape or size.

In each of the above two embodiments, the mounting base 1 is provided with an interface 7 to be connected with a surgical tool and/or a surgical robot.

Based on the above embodiments, the present invention further includes variations of the above embodiments. For example, the number of the supporting faces 2 may be three, four or five, and two or four reflective balls 3 are mounted on each of the supporting faces 2, and a positioning face 5 is formed by a quadrilateral with the four reflective balls 3 on the same supporting face 2 or on the two adjacent supporting faces 2 as end points. Moreover, the reflective balls 3 and their mounting ways in Embodiment 1 and Embodiment 2 are interchangeable. In addition, the present invention can also be applied onto other devices or instruments in the surgical navigation system that requires positioning by changing the shape of the mounting base 1 or by changing the interface 7 arranged for connecting.

In combination with the structure of the present invention, by means of a matched control program, the definition of the tool in the present invention is characterized in that: when the number of the reflective balls 3 mounted on a single supporting face 2 is "4", the supporting face 2 is defined as a separated positioning face 5 in the definition of the tool; when the number of the reflective balls 3 mounted on the single supporting face 2 is "2", the adjacent two supporting faces 2 are collectively defined as one positioning face 5 and each supporting face 2 can be shared by different positioning faces 5 in the definition of the tool. When the present invention is implemented, the positions and the geometric sizes of the four reflective balls mounted are generated by a programmed positioning face generating algorithm, and finally the mutual differences between the two positioning faces are detected by the tool-specific detection software on the basis of the generated data so as to ensure that the designed tool meets the specificity requirements of optical positioning systems.

The above embodiments are merely used for illustrating the objects, technical solutions and beneficial effects of the present invention in further detail, and are not intended to limit the present invention. Any modifications, equivalent substitutions, improvements and the like made within the spirit and principle of the present invention should be included in the protection scope of the present invention.

The invention claimed is:

1. An optical tracking tool for navigating a surgery, comprising:

a mounting base, wherein the mounting base is provided with two to six supporting faces thereon; and at least two positioning faces, each of the at least two positioning faces formed by four reflective balls located on a same supporting face or four reflective balls located on two adjacent supporting faces, wherein an included angle between surface normal vectors of two adjacent positioning faces of the at least two positioning faces is 90°-140°, wherein any two of the at least two positioning faces are different in shape or size, wherein each of the reflective balls is fixed on one of the supporting faces through corresponding reflective ball mounting bases;

wherein each of the reflective ball mounting bases comprises a ball support, a seal rubber ring and an annular cover plate, and each of the ball supports is fixedly connected to one of the two to six supporting faces; and wherein each of the reflective balls is composed of two hemispheres with different diameters, wherein for each reflective ball, a larger-diameter hemispherical portion of the reflective ball is held up by the ball support and then is locked and fastened by the annular cover plate arranged on the ball support in a form of a buckle, a smaller-diameter hemispherical portion of the reflective ball protrudes from the annular cover plate, and the seal rubber ring is arranged between the ball support and the larger-diameter hemispherical portion of the reflective ball.

2. The optical tracking tool for navigating a surgery according to claim 1, wherein the mounting base is provided with an interface to be connected with a surgical tool and/or a surgical robot.

* * * * *